(12) United States Patent
Funkhouser

(10) Patent No.: US 10,413,654 B2
(45) Date of Patent: Sep. 17, 2019

(54) ACCESS DISCONNECTION SYSTEM AND METHOD USING SIGNAL METRICS

(71) Applicants:Baxter International Inc., Deerfield, IL (US); Baxter Healthcare SA, Glattpark (Opfikon) (CH)

(72) Inventor: Chloe Marie Funkhouser, Libertyville, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 474 days.

(21) Appl. No.: 14/978,954

(22) Filed: Dec. 22, 2015

(65) Prior Publication Data

US 2017/0173253 A1   Jun. 22, 2017

(51) Int. Cl.
*A61M 1/36* (2006.01)
*A61M 1/14* (2006.01)

(52) U.S. Cl.
CPC ............ *A61M 1/3656* (2014.02); *A61M 1/14* (2013.01); *A61M 1/3639* (2013.01); *A61M 1/3653* (2013.01); *A61M 2205/15* (2013.01); *A61M 2205/16* (2013.01); *A61M 2205/17* (2013.01); *A61M 2205/18* (2013.01);
(Continued)

(58) Field of Classification Search
CPC .... A61M 1/14; A61M 1/3653; A61M 1/3656; A61M 1/3639; A61M 2205/15; A61M 2205/3317; A61M 2205/3375; A61M 2205/3592
See application file for complete search history.

(56) References Cited

U.S. PATENT DOCUMENTS 3,882,861 A   5/1975   Kettering et al.
3,946,731 A   3/1976   Lichtenstein
(Continued)

FOREIGN PATENT DOCUMENTS

DE   196 09 698   9/1997
DE   198 48 235   3/2000
(Continued)

OTHER PUBLICATIONS

International Search Report for PCT/US2016/066883 dated Mar. 17, 2017.
(Continued)

*Primary Examiner* — Benjamin J Klein
(74) *Attorney, Agent, or Firm* — K&L Gates LLP

(57) ABSTRACT

Renal failure therapy system includes a blood filter, a blood pump, a dialysis fluid pump, a blood line connecting to a patient, a transmitter for receiving a transmit signal and transmitting a wave into blood flowing through the blood line, a receiver for receiving the wave and emitting a corresponding received signal, and a processor for initiating the transmit signal and for receiving the received signal, configured to convert the transmit and received signals into a frequency domain, extract spectral values for the converted transmit and received signals, calculate at least one of a reflection coefficient (R) or an impedance ratio (I) using the spectral values, and analyze an imaginary part of at least one of R or I to determine if an access disconnection event concerning fluid communication between the blood line and the patient has occurred.

24 Claims, 9 Drawing Sheets

(52) U.S. Cl.
CPC .............. *A61M 2205/3317* (2013.01); *A61M 2205/3375* (2013.01); *A61M 2205/3592* (2013.01)

(56) References Cited

U.S. PATENT DOCUMENTS

| | | | |
|---|---|---|---|
| 4,185,641 A | 1/1980 | Minior et al. | |
| 4,239,047 A | 12/1980 | Griggs, III et al. | |
| 4,277,227 A | 7/1981 | Jenkins | |
| 4,353,368 A | 10/1982 | Slovak et al. | |
| 4,392,847 A | 7/1983 | Whitney et al. | |
| 4,450,527 A | 5/1984 | Sramek | |
| 4,501,483 A | 2/1985 | Romansky et al. | |
| 4,534,756 A | 8/1985 | Nelson | |
| 4,541,282 A | 9/1985 | Auerweck et al. | |
| 4,648,869 A | 3/1987 | Bobo, Jr. | |
| 4,710,163 A | 12/1987 | Butterfield | |
| 4,828,543 A | 5/1989 | Weiss et al. | |
| 4,846,792 A | 7/1989 | Bobo, Jr. et al. | |
| 4,923,598 A | 5/1990 | Schal | |
| 4,959,050 A | 9/1990 | Bobo, Jr. | |
| 4,972,826 A | 11/1990 | Koehler et al. | |
| 4,979,940 A | 12/1990 | Bobo, Jr. et al. | |
| 4,981,467 A | 1/1991 | Bobo, Jr. et al. | |
| 5,026,348 A | 6/1991 | Venegas | |
| 5,100,374 A | 3/1992 | Kageyama | |
| 5,146,414 A | 9/1992 | McKown et al. | |
| 5,311,871 A | 5/1994 | Yock | |
| 5,427,695 A | 6/1995 | Brown | |
| 5,557,263 A | 9/1996 | Fisher et al. | |
| 5,693,008 A | 12/1997 | Brugger et al. | |
| 5,790,036 A | 8/1998 | Fisher et al. | |
| 5,830,365 A | 11/1998 | Schneditz | |
| 5,863,421 A | 1/1999 | Peter, Jr. et al. | |
| 5,910,252 A | 6/1999 | Truitt et al. | |
| 6,066,261 A | 5/2000 | Spickermann | |
| 6,071,421 A | 6/2000 | Brown | |
| 6,077,443 A | 6/2000 | Goldau | |
| 6,090,048 A | 7/2000 | Hertz et al. | |
| 6,167,765 B1 | 1/2001 | Weitzel | |
| 6,187,199 B1 | 2/2001 | Goldau | |
| 6,200,485 B1 | 3/2001 | Kitaevich et al. | |
| 6,221,040 B1 | 4/2001 | Kleinekofort | |
| 6,337,049 B1 | 1/2002 | Tamari | |
| 6,572,576 B2 | 6/2003 | Brugger et al. | |
| 6,575,927 B1 | 6/2003 | Weitzel et al. | |
| 6,595,942 B2 | 7/2003 | Kleinekofort | |
| 6,623,443 B1 | 9/2003 | Polaschegg | |
| 6,649,063 B2 | 11/2003 | Brugger et al. | |
| 6,663,585 B1 | 12/2003 | Ender | |
| 6,730,055 B2 | 5/2004 | Bainbridge et al. | |
| 6,736,789 B1 | 5/2004 | Spickermann | |
| 6,767,333 B1 | 6/2004 | Muller et al. | |
| 6,773,670 B2 | 8/2004 | Stringer et al. | |
| 6,780,159 B2 | 8/2004 | Sandler et al. | |
| 6,804,991 B2 | 10/2004 | Balschat et al. | |
| 6,827,698 B1 | 12/2004 | Kleinekofort | |
| 6,880,404 B2 | 4/2005 | Uberreiter | |
| 6,899,691 B2 | 5/2005 | Bainbridge et al. | |
| 6,979,306 B2 | 12/2005 | Moll | |
| 7,040,142 B2 | 5/2006 | Burbank | |
| 7,060,047 B2 | 6/2006 | Lodi et al. | |
| 7,087,033 B2 | 8/2006 | Brugger et al. | |
| 7,169,352 B1 | 1/2007 | Felt et al. | |
| 7,172,569 B2 | 2/2007 | Kleinekofort | |
| 7,172,570 B2 | 2/2007 | Cavalcanti et al. | |
| 7,276,041 B2 | 10/2007 | Moll | |
| 7,410,473 B2 | 8/2008 | Levin et al. | |
| 7,537,687 B2 | 5/2009 | Toyoda et al. | |
| 7,615,028 B2 | 11/2009 | O'Mahony | |
| 8,152,751 B2 | 4/2012 | Roger et al. | |
| 8,197,421 B2 | 6/2012 | Freeman et al. | |
| 8,197,431 B2 * | 6/2012 | Bennison ............ | A61M 1/3653 600/462 |
| 8,603,020 B2 * | 12/2013 | Roger ................. | A61M 1/3653 604/4.01 |
| 2001/0007930 A1 | 7/2001 | Kleinekofort | |
| 2002/0004636 A1 | 1/2002 | Tsubata | |
| 2002/0198483 A1 | 12/2002 | Wariar et al. | |
| 2003/0009123 A1 | 1/2003 | Brugger et al. | |
| 2003/0128125 A1 | 7/2003 | Burbank et al. | |
| 2003/0130607 A1 | 7/2003 | Delvano et al. | |
| 2003/0152482 A1 | 8/2003 | O'Mahony et al. | |
| 2004/0030277 A1 | 2/2004 | O'Mahony et al. | |
| 2004/0041792 A1 | 3/2004 | Criscione | |
| 2004/0171977 A1 | 9/2004 | Paolini et al. | |
| 2004/0186409 A1 | 9/2004 | Cavalcanti et al. | |
| 2004/0228760 A1 | 11/2004 | Stringer et al. | |
| 2005/0004502 A1 | 1/2005 | O'Mahony et al. | |
| 2005/0010118 A1 | 1/2005 | Toyoda et al. | |
| 2005/0131332 A1 | 6/2005 | Kelly et al. | |
| 2005/0230313 A1 | 10/2005 | O'Mahony et al. | |
| 2006/0081517 A1 | 4/2006 | Toyoda et al. | |
| 2006/0122552 A1 | 6/2006 | O'Mahony | |
| 2007/0004996 A1 | 1/2007 | Lovejoy et al. | |
| 2007/0004997 A1 | 1/2007 | Felt et al. | |
| 2007/0010779 A1 | 1/2007 | Utterberg et al. | |
| 2007/0078368 A1 | 4/2007 | Felt et al. | |
| 2007/0093774 A1 | 4/2007 | Felt et al. | |
| 2007/0108128 A1 | 5/2007 | Koperschmidt et al. | |
| 2007/0112289 A1 | 5/2007 | Cavalcanti et al. | |
| 2007/0179433 A1 | 8/2007 | Jonsson et al. | |
| 2007/0232980 A1 | 10/2007 | Felt et al. | |
| 2008/0183120 A1 | 1/2008 | Utterberg et al. | |
| 2008/0108930 A1 | 5/2008 | Weitzel et al. | |
| 2008/0171960 A1 | 7/2008 | Brieske et al. | |
| 2008/0195022 A1 | 8/2008 | Lucke et al. | |
| 2008/0214979 A1 | 9/2008 | Brugger et al. | |
| 2011/0046533 A1 | 2/2011 | Stefani et al. | |
| 2011/0160637 A1 * | 6/2011 | Beiriger ............ | A61M 1/3653 604/6.11 |
| 2014/0298891 A1 * | 10/2014 | Holmer ............ | A61M 1/3639 73/37 |
| 2015/0080782 A1 | 3/2015 | Roger et al. | |

FOREIGN PATENT DOCUMENTS

| | | |
|---|---|---|
| DE | 102009007806 | 8/2010 |
| EP | 0 121 931 | 10/1984 |
| EP | 0 232 599 | 8/1987 |
| EP | 0 300 315 | 1/1989 |
| EP | 0 332 330 | 9/1989 |
| EP | 0 361 793 | 4/1990 |
| EP | 0 895 787 | 2/1999 |
| EP | 1 472 973 | 11/2004 |
| EP | 1 736 185 | 12/2006 |
| EP | 2442725 | 4/2012 |
| JP | 11104233 | 4/1999 |
| JP | 2005040518 | 2/2005 |
| JP | 2006/110118 | 4/2006 |
| JP | 2006/110120 | 4/2006 |
| WO | WO 91/00113 | 1/1991 |
| WO | WO 97/10013 | 3/1997 |
| WO | WO 99/29356 | 6/1999 |
| WO | WO 00/18451 | 4/2000 |
| WO | WO 02/102441 | 12/2002 |
| WO | WO 03/002174 | 1/2003 |
| WO | WO 03/006944 | 1/2003 |
| WO | WO 03/058567 | 1/2003 |
| WO | WO 03/058608 | 1/2003 |
| WO | WO2005/019416 | 3/2005 |
| WO | WO 2006/122001 | 11/2006 |

OTHER PUBLICATIONS

Written Opinion of the International Preliminary Examining Authority for PCT/US2016/066883 dated Aug. 7, 2017.

Wabel et al., Ansätze zur Identifikation von Patientenparametern während der Hämodialysetherapie, Identification of Patient Parameters during Hemodialysis, vol. 50, Issue May 2002 (May 2002) pp.

(56) References Cited

OTHER PUBLICATIONS 220-227 ISSN (Print) 0178-2312, Published Online Sep. 25, 2009—English Translation—11 pages.

* cited by examiner

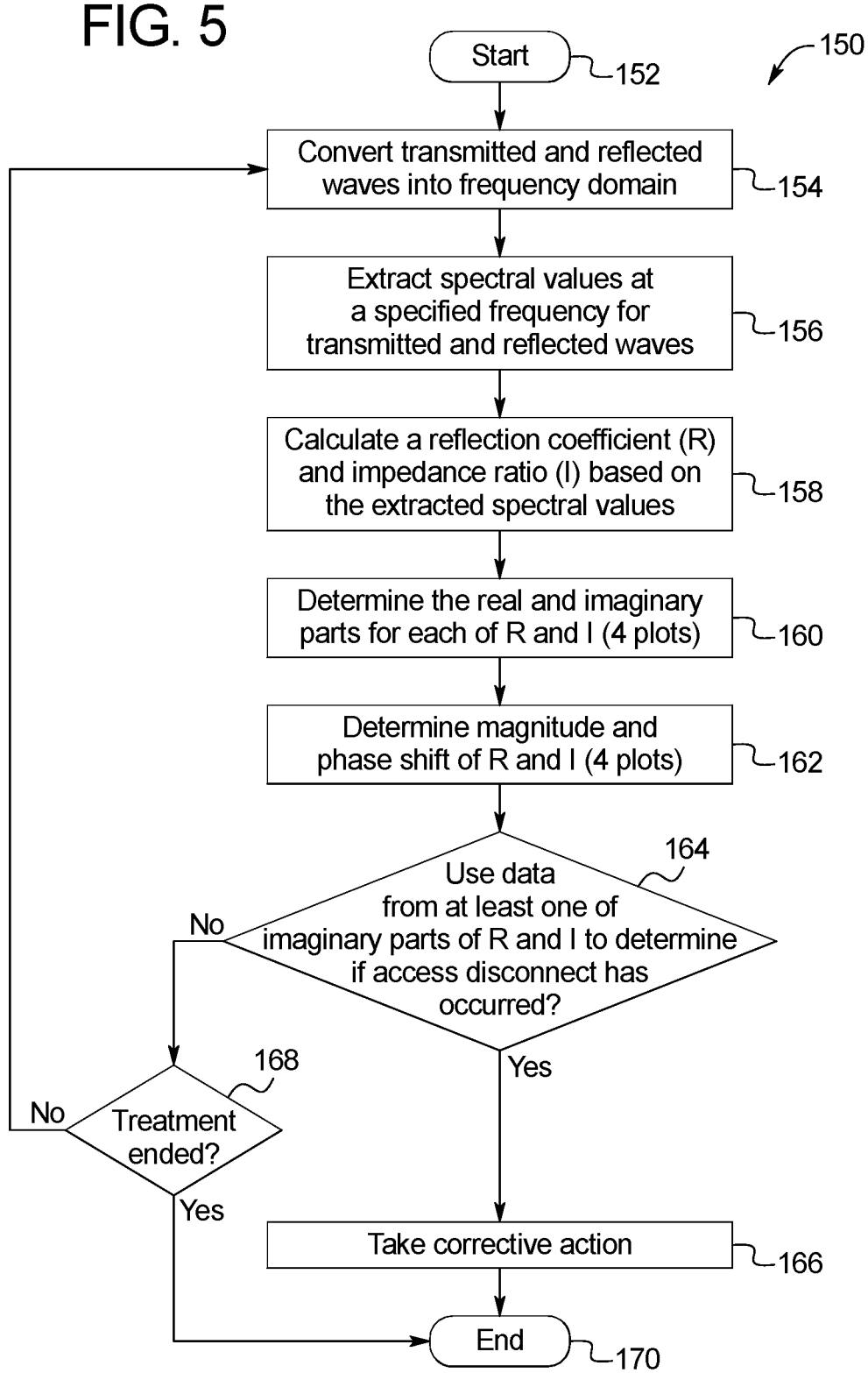

ACCESS DISCONNECTION SYSTEM AND METHOD USING SIGNAL METRICS

CROSS-REFERENCE TO RELATED APPLICATIONS

This application is related in subject matter to commonly owned (i) U.S. Pat. No. 9,138,528, issued Sep. 22, 2015, entitled "Acoustic Access Disconnection Systems and Methods", filed Dec. 4, 2013; (ii) U.S. Pat. No. 8,603,020, issued Dec. 10, 2013, entitled "Ultrasound Access Disconnection Systems and Methods", filed Feb. 20, 2012; (iii) U.S. Pat. No. 8,197,431, issued Jun. 12, 2012, entitled, "Acoustic Access Disconnect Detection System", filed Sep. 21, 2007, and (iv) U.S. Pat. No. 8,152,751, issued Apr. 10, 2012, entitled "Acoustic Access Disconnection Systems and Methods", filed Feb. 9, 2007.

BACKGROUND

The present disclosure relates generally to patient access disconnection systems and methods for medical treatments. More specifically, the present disclosure relates to the detection of a patient access disconnection, such as the detection of needle or catheter dislodgment during dialysis therapy.

A variety of different medical treatments relate to the delivery of fluid to, through and/or from a patient, such as the delivery of blood between a patient and an extracorporeal system connected to the patient via a needle or needles inserted within the patient. For example, plasmapherisis, hemodialysis, hemofiltration and hemodiafiltration are all treatments that remove waste, toxins and excess water directly from the patient's blood. During these treatments, the patient is connected to an extracorporeal circuit and a machine, while the patient's blood is pumped through the circuit and machine. Waste, toxins and excess water are removed from the patient's blood, after which the blood is returned to the patient.

In the above treatments, needles or similar access devices are inserted into the patient's vascular system, so that the patient's blood can be transported to and from the extracorporeal machine. Traditional hemodialysis, hemofiltration and hemodiafiltration treatments can last several hours and are performed typically in treatment centers three or four times per week. In the in-center treatments, nurses monitor the patients to detect needle dislodgment. Nevertheless, a needle may not be in plain view of the patient or medical staff (e.g., it may be covered by a blanket) such that it is not readily visible.

Moreover, in view of the increased quality of life, observed reductions in both morbidity and mortality, and lower costs with respect to in-center treatments, a renewed interest has arisen for self-care and home treatments, such as home hemodialysis. Home treatments may be performed during the day, evening or nocturnally. If unsupervised or asleep, dislodgment risks increase because a caregiver is not present, while patient may not be aware of the dislodgment.

FIG. 1 illustrates a known access disconnection configuration. Blood is drawn from an arm 12 of a patient through an arterial line 14 connected to the patient via an arterial needle 14b. Blood is returned to patient 12 after it has been treated via a venous line 16 and venous needle 16b. Needles 14b and 16b connect to a shunt 12a, which is placed in fluid communication with one of the patient's veins. Accidental disconnection of the arterial line 14 during treatment is not as serious an issue because this situation simply eliminates the source of blood to the blood pump. Access disconnection of venous line 16 during treatment is a serious concern however because arterial line 14 keeps feeding blood to the blood pump, while venous line 16 returns blood to a location outside of patient 12.

Various systems exist for detecting needle dislodgement in hemodialysis. For example, U.S. Pat. No. 7,022,098 ("the '098 Patent") and U.S. Pat. No. 7,052,480 ("the '480 Patent"), both entitled Access Disconnection Systems And Methods, and assigned to the assignee of the present application, disclose access disconnection systems that measure an electrical impedance of the extracorporeal dialysis circuit connected to the vascular access needles. An external voltage or current source injects a small current (e.g., less that 2.5 μ-Amp) into the blood flow. Measures are taken to ensure that the current does not exceed 10μ-Amp, which is considered in the art to be a safety limit for intercardiac devices. Such a small current however can be hard to detect. Further, impedance detection sensitivity may be decreased when the patient is connected by accident to earth ground.

Another problem with systems that inject current into the extracorporeal circuits occurs if the dislodged needle reestablishes contact with the other needle physically or through leaked blood. Here, the electrical parameter being sensed, e.g., impedance, may not change or not change enough to signal an access disconnection even though one has occurred.

A further obstacle involves the addition of electrical contacts to the disposable portion of the blood treatment system. Metal or otherwise conductive members placed in the disposable add manufacturing difficulty and cost.

A need accordingly exists for improved blood access disconnection systems.

SUMMARY

The examples described herein disclose access disconnection systems and methods applicable, for example, to: plasmapherisis, hemodialysis ("HD"), hemofiltration ("HF") and hemodiafiltration ("HDF"). The access disconnection systems may also be used with continuous renal replacement therapy ("CRRT") treatments, which also require vascular access. The access disconnection examples below operate with systems having a diffusion membrane or filter, such as a dialyzer, e.g., for HD or HDF, or a hemofilter, e.g., for HF or CRRT. Each of HD, HF, HDF and CRRT may be referred to herein for convenience as a renal failure therapy.

Moreover, each of the systems described herein may be used with clinical or home-based machines. For example, the systems may be employed in in-center HD, HF or HDF machines, which run throughout the day. Alternatively, the systems may be used with home HD, HF or HDF machines, which are operated at the patient's convenience. One such home system is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignee of the present application. Another such home system is described in U.S. Pat. No. 8,721,884 ("the '884 Patent"), issued May 13, 2014, entitled "Hemodialysis Systems and Methods", filed Feb. 7, 2013. The entire contents of both of the above references are incorporated herein by reference and relied upon.

The access disconnection examples below may operate with systems having bagged or batch dialysis fluid supplies, which may include a single bag or multiple bags of dialysis fluid ganged together and used one after another. Alternatively, each of the access disconnection systems shown below may be used with a machine having an on-line source, such as one or more concentrate pump configured to combine one or more concentrate (liquid or solid) with water to form dialysis fluid on-line.

Various non-invasive access disconnection systems are described herein. The systems do not require a voltage or current to be injected into the blood circuit, which illuminates problems with sensitivity and patient grounding inherent in impedance sensing systems. Because the present systems do not rely on the connection or disconnection of an electrical loop, they are immune from the reestablishment of a conductive path with a dislodged needle via blood loss. The disclosed systems in various embodiments communicate with a controller of the dialysis machine via wired or wireless connection. The addition of structure to the disposable tubing and/or cassette that the corresponding machine uses may therefore be minimal or non-existent, which is desirable from cost and complexity standpoints.

In one embodiment, a renal failure therapy (HD, HF, HDF or CRRT) machine includes a wave transmitter and receiver. As used herein, a "transducer" is generally a device that converts an electrical signal (voltage or current) into a wave (e.g., acoustic, ultrasonic) or vice versa, converting the wave into an electrical signal. The transmitter and receiver can be a single transducer that at one time is used as an emitter, converting an electrical signal into a desired wave, and at another time is a receiver, converting a received wave into an output electrical signal. The transmitter and receiver can alternatively include an emitting transducer that is dedicated to converting an electrical signal into a desired wave and a separate receiving transducer that is dedicated to converting a received wave into an output electrical signal. In either case, a desired wave has a desired frequency in one embodiment, which can be an acoustic or ultrasonic frequency.

In various embodiments, the one or more transducer may be, for example, piezoelectric, piezoresistive, magnetic, electroaucoustic, electromagnetic, inductive, capacitive, or resistive.

The wave transmitter and receiver is provided in one embodiment on the chassis of a renal failure therapy machine, such as ones disclosed in the above-incorporated patents. The machines typically have an arterial line running from the patient to a blood pump on the machine and a venous line running from a blood filter (dialyzer or hemofilter) to the patient. The wave transmitter is placed on the machine so that the venous line can be clamped up against the transmitter in one embodiment. As discussed above, the venous line is the important blood line to monitor in one embodiment because it returns blood to the patient, thus its dislodgement could lead to the blood being returned instead to a place outside the patient.

The wave transmitter and receiver is provided in another embodiment at a downstream location on the venous line. Here, a small housing holds the transmitter and receiver (single or dual transducer) along with other electronics. The housing includes structure, such as a clip or overlapping flaps that allow the housing to be removeably coupled at a desired location to the venous line. The other electronics can include processing, memory and electronics needed to communicate wired or wirelessly with a processor of the renal failure therapy machine, such as a main control processor. One reason to locate the transmitter and receiver downstream on the venous line may be to avoid noise generated at the machine and/or to receive a stronger reflected signal.

The signal is reflected off of the needle access point of the venous needle in one embodiment. If the venous needle becomes dislodged from the patient, the reflected signal changes, which is sensed and acted upon. For example, the machine can shut down treatment, place itself into a safe mode, and alarm the patient. If the patient can restore the venous access, it may be possible to continue the same treatment. Alternatively, treatment is shut down for good, and the patient is instructed to fully disconnect himself or herself from the machine.

The system includes software and electronics configured to analyze the transmitted (or incident) and reflected signals. The software and electronics are provided in one embodiment on a main processor of the renal failure therapy machine. In an alternative embodiment, the software and electronics are provided on a user interface or ("UI") processor of the renal failure therapy machine. In an embodiment in which a housing holding the transmitter and receiver (single or dual transducer) is provided at a downstream location on the venous line, the software and electronics may, but does not have to, be provided in the housing. In a further alternative embodiment, the software and electronics may be provided redundantly at a first processor, e.g., the main control processor and at a second processor, e.g., at a safety processor. Here, the machine can shut down treatment, place itself into a safe mode, and alarm the patient if either of the redundant processors detects a needle dislodgement.

It is also contemplated to combine the software and electronics configured to analyze the reflected signal with any one or more other type of access disconnection system ("ADS") to produce a hybrid redundant system. For example, the software and electronics configured to analyze the reflected signal may be combined with any of the electrical impedance type ADS systems incorporated by reference above.

The software and electronics in an embodiment take a Fourier transform of the incident and reflected signals. Since the Fourier transform is a complex-valued function, taking the Fourier transform of the incident and reflected signals yields real and imaginary parts for the Fourier transform spectrum for each signal. Real and imaginary parts are parts of a complex number z, where $z=x+iy$, where x is the real part of z, y is the imaginary part of z, and i is the square root of −1.

The software and electronics then determine the Fourier transform spectral value (a complex number z) for each of the signals at a specified frequency. The software and electronics uses the spectral values to calculate a reflection coefficient (R) and impedance ratio (I), which are in turn analyzed for a needle dislodgment.

Because the reflection coefficient (R) and the impedance ratio (I) are calculated from complex components (the real (x) and imaginary parts (y) of the spectral values (z)), R and I are likewise complex numbers z. Thus R and I each has its own real part x and imaginary part y. The software and electronics of the present disclosure are further configured to calculate a magnitude and phase shift from the real and imaginary parts of each of the reflection coefficient (R) and the impedance ratio (I).

Illustrated below are eight charts showing different signal evaluations for a same simulated venous dislodgement event versus time using the above-described venous line transmitted and reflected signals, e.g., acoustic signals. The eight plots include (i) a plot of the real part of the reflection coefficient (R) versus time, (ii) a plot of the real part of the impedance ratio (I) versus time, (iii) a plot of the magnitude of the reflection coefficient (R) versus time, (iv) a plot of the magnitude of the impedance ratio (I) versus time, (v) a plot of the imaginary part of the reflection coefficient (R) versus time, (vi) a plot of the imaginary part of the impedance ratio (I) versus time, (vii) a plot of the phase shift of the reflection coefficient (R) versus time, and (viii) a plot of the phase shift of the impedance ratio (I) versus time.

Of the eight different plots, plots (v) to (viii) show the best signal to noise ratio. It is accordingly contemplated for the software and electronics to look to any one, or more, or all of the data of plots (v) to (viii) to determine if an access disconnection event has taken place. In other alternative embodiments, the software and electronics to look to any one, or more, or all of the data of plots (i) to (iv) in combination with any one, or more, or all of the data of plots (v) to (viii) to determine if an access disconnection event has taken place.

In light of the technical features set forth herein, and without limitation, in a first aspect, a renal failure therapy system includes: a blood filter; a blood pump in fluid communication with the blood filter; a dialysis fluid pump in fluid communication with the blood filter; a blood line for connection to a patient, the blood line in fluid communication with the blood filter; a transmitter positioned and arranged to receive a transmit signal and to transmit a wave into blood flowing through the blood line, the wave based on the transmit signal; a receiver positioned and arranged to receive the wave and to emit a received signal based on the received wave; and at least one processor for initiating the transmit signal and for receiving the received signal, the processor configured to convert the transmit and received signals into a frequency domain, extract spectral values for the converted transmit and received signals, calculate at least one of a reflection coefficient (R) or an impedance ratio (I) using the spectral values, and analyze an imaginary part of at least one of R or I to determine if an access disconnection event concerning fluid communication between the blood line and the patient has occurred.

In a second aspect, which may be used in combination with any other aspect described herein unless specified otherwise, the at least one processor analyzes imaginary parts of both the reflection coefficient (R) and the impedance ratio (I) to determine if an access disconnection event concerning fluid communication between the blood line and the patient has occurred.

In a third aspect, which may be used in combination with any other aspect described herein unless specified otherwise, the at least one processor further analyzes at least one of a real part of at least one of R or I, a phase shift of at least one of R or I, or a magnitude of at least one of R or I to determine if an access disconnection event concerning fluid communication between the blood line and the patient has occurred.

In a fourth aspect, which may be used in combination with the third aspect and any other aspect described herein unless specified otherwise, the phase shift is provided as an angular value in degrees.

In a fifth aspect, which may be used in combination with any other aspect described herein unless specified otherwise, the external spectral values each include a real and an imaginary part, leading to the imaginary parts of R and I.

In a sixth aspect, which may be used in combination with any other aspect described herein unless specified otherwise, the spectral values are calculated at a specified frequency.

In a seventh aspect, which may be used in combination with the sixth aspect and any other aspect described herein unless specified otherwise, the specified frequency is in a range of 10 Hz to 12 Hz.

In an eighth aspect, which may be used in combination with the sixth aspect and any other aspect described herein unless specified otherwise, the specified frequency is determined based on empirical testing.

In a ninth aspect, which may be used in combination with any other aspect described herein unless specified otherwise, the at least one processor determines at least one baseline value for analysis during a period of time at the beginning of a treatment.

In a tenth aspect, which may be used in combination with any other aspect described herein unless specified otherwise, the converted transmit and received signals each include real and imaginary parts, leading to the imaginary parts of R and I.

In an eleventh aspect, which may be used in combination with any other aspect described herein unless specified otherwise, the imaginary parts of the reflection coefficient (R) and the impedance ratio (I) are provided as unitless numerical values.

In a twelfth aspect, which may be used in combination with any other aspect described herein unless specified otherwise, the renal failure therapy system is a plasmapheresis, hemodialysis ("HD"), hemofiltration ("HF"), hemodiafiltration ("HDF") or continuous renal replacement therapy ("CRRT") system, and wherein the blood filter is a dialyzer or hemofilter.

In a thirteenth aspect, which may be used in combination with any other aspect described herein unless specified otherwise, the blood filter, the blood pump, and the dialysis fluid pump are housed in a machine, and the transmitter and the receiver are housed in a separate unit that communicates wirelessly with the machine.

In a fourteenth aspect, which may be used in combination with any other aspect described herein unless specified otherwise, the blood filter, the blood pump, and the dialysis fluid pump are housed in a machine, and the transmitter and the receiver are located at the machine.

In a fifteenth aspect, which may be used in combination with any other aspect described herein unless specified otherwise, the at least one processor is part of a housing for the transmitter and the receiver, the housing configured to be attached to the blood line.

In a sixteenth aspect, which may be used in combination with any other aspect described herein unless specified otherwise, the at least one processor is a first processor, and which includes a second, redundant at least one processor for receiving the transmit and received signals, the second processor configured to convert the transmit and received signals into the frequency domain, extract spectral values for the converted transmit and received signals, calculate at least one of a reflection coefficient (R) or an impedance ratio (I) using the spectral values, and analyze an imaginary part at least one of R or I to determine if an access disconnection event concerning fluid communication between the blood line and the patient has occurred.

In a seventeenth aspect, which may be used in combination with any other aspect described herein unless specified otherwise, the blood line is a venous blood line.

In an eighteenth aspect, which may be used in combination with any other aspect described herein unless specified otherwise, wherein the renal failure therapy system upon the disconnection output is configured to perform at least one of: (i) shutting down a blood pump, (ii) activating a venous line clamp, and (iii) alerting the patient of the disconnection.

In a nineteenth aspect, which may be used in combination with any other aspect described herein unless specified otherwise, the transmitter and the receiver are of at least one type selected from the group consisting of: a single transducer, multiple transducers, piezoelectric, electromagnetic, or any suitable combination thereof.

In a twentieth aspect, which may be used in combination with any other aspect described herein unless specified otherwise, the disconnection output is of at least one type selected from the group consisting of: an electrical output, a radio frequency output, a microwave output, a continuous output, an intermittent output, an output occurring upon the change, a wireless output, or any suitable combination thereof.

In a twenty-first aspect, which may be used in combination with any other aspect described herein unless specified otherwise, a renal failure therapy system includes: a blood filter; a blood pump in fluid communication with the blood filter; a dialysis fluid pump in fluid communication with the blood filter; a blood line for connection to a patient, the blood line in fluid communication with the blood filter; a transmitter positioned and arranged to receive a transmit signal and to transmit a wave into blood flowing through the blood line, the wave based on the transmit signal; a receiver positioned and arranged to receive the wave and to emit a received signal based on the received wave; and at least one processor for initiating the transmit signal and for receiving the received signal, the processor configured to convert the transmit and received signals into a frequency domain, extract spectral values for the converted transmit and received signals, calculate at least one of a reflection coefficient (R) or an impedance ratio (I) using the spectral values, and analyze plural ones of (i) an imaginary part of R, (ii) an imaginary part of I, (iii) a phase shift of R, (iv) a phase shift of I, (v) a real part of R, (vi) a real part of I, (vii) a magnitude of R, and (viii) a magnitude of I, and apply an algorithm to the analyzed plural ones of (i) to (viii) to determine if an access disconnection event concerning fluid communication between the blood line and the patient has occurred.

In a twenty-second aspect, which may be used with the twenty-first aspect in combination with any other aspect described herein unless specified otherwise, the algorithm includes determining that an access disconnection event concerning fluid communication between the blood line and the patient has occurred if any of the plural ones of (i) to (viii) indicates the access disconnection event.

In a twenty-third aspect, which may be used with the twenty-first aspect in combination with any other aspect described herein unless specified otherwise, the algorithm includes determining that an access disconnection event concerning fluid communication between the blood line and the patient has occurred if each of the plural ones of (i) to (viii) indicates the access disconnection event.

In a twenty-fourth aspect, which may be used with the twenty-first aspect in combination with any other aspect described herein unless specified otherwise, the algorithm includes determining that an access disconnection event concerning fluid communication between the blood line and the patient has occurred if multiple ones of the plural ones of (i) to (viii) indicate the access disconnection event.

In a twenty-fifth aspect, any of the features, functionality and alternatives described in connection with any one or more of FIGS. 1 to 6H may be combined with any of the other aspects listed herein, and any of the features, functionality and alternatives described in connection with any of the other one or more of FIGS. 1 to 6H.

In light of the above aspects and the present disclosure, it is therefore an advantage of the present disclosure to provide an improved access disconnection system and method for renal failure therapy machines.

It is another advantage of the present disclosure to provide non-invasive access disconnection systems methods.

It is a further advantage of the present disclosure to provide access disconnection systems and methods that do not induce current into the patient's blood.

It is still another advantage of the present disclosure to provide access disconnection systems and methods that do not add (or not add significantly) to disposable cost or manufacture.

It is still a further advantage of the present disclosure to provide access disconnection systems and methods that avoid problems from to electrical reconnection due to lost blood.

It is yet another advantage of the present disclosure to provide access disconnection systems and methods that are robust and quick acting.

It is yet a further advantage of the present disclosure to provide access disconnection systems and methods that are compatible with blood needle and/or catheter applications.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 5 is a process flow diagram illustrating one access disconnection method embodiment of the present disclosure.

DETAILED DESCRIPTION

System Hardware

The examples described herein are applicable to any medical fluid therapy system requiring vascular access. The examples are particularly well suited for the control of kidney failure therapies, such as all forms of hemodialysis ("HD"), hemofiltration ("HF"), hemodiafiltration ("HDF") and continuous renal replacement therapies ("CRRT") requiring vascular access, referred to herein collectively or generally individually as renal failure therapy. Moreover, the machines and any of the access disconnection systems and methods described herein may be used in clinical or home settings. For example, the machine and the access disconnection systems may be employed in an in-center HD machine, which runs virtually continuously throughout the day. Alternatively, they may be used in a home HD machine, which can for example be run at night while the patient is sleeping. Moreover, each of the vascular disconnection examples described herein may include a diffusion membrane or filter, such as a dialyzer, e.g., for HD or HDF, or a hemofilter, e.g., for HF.

Figure 1:
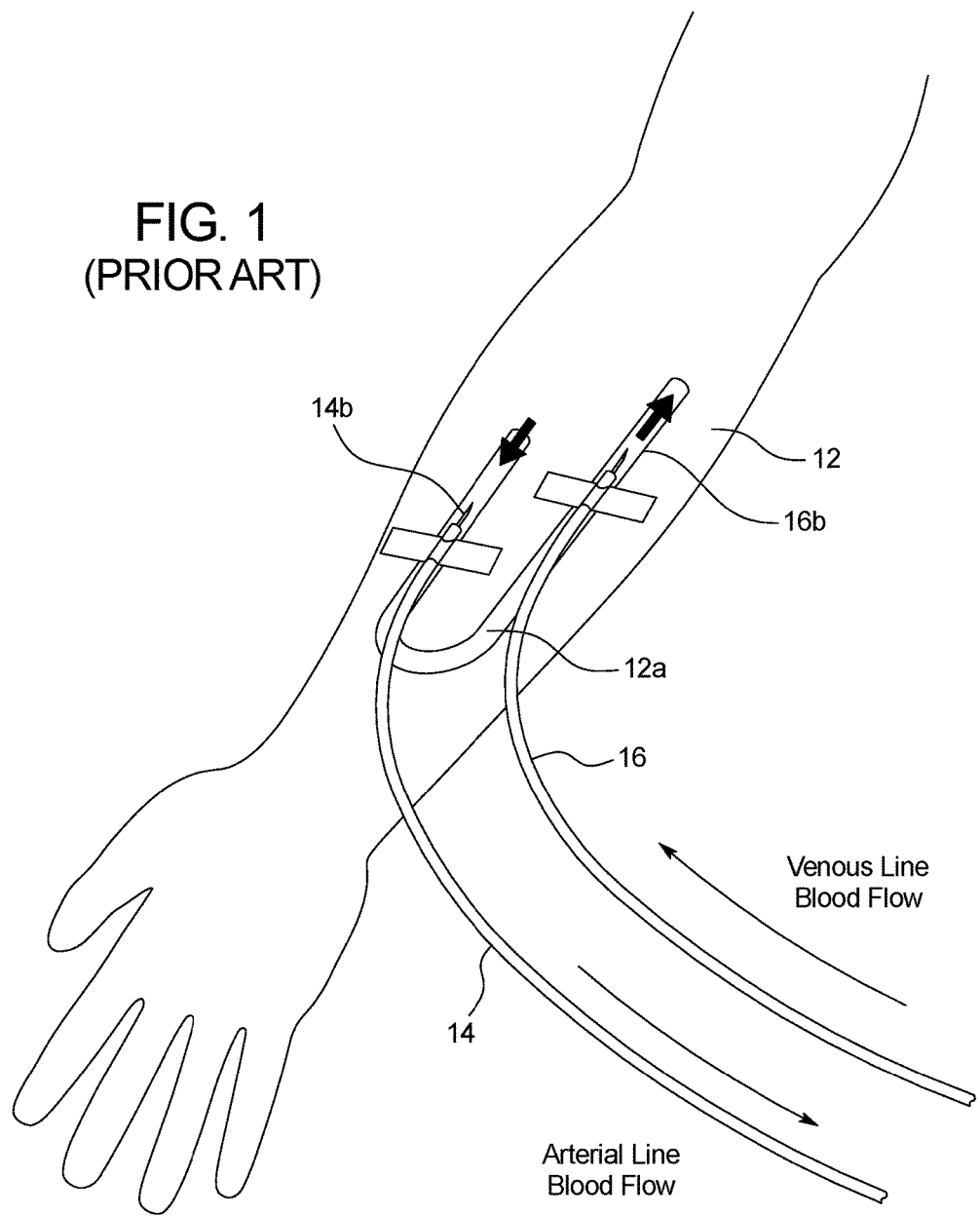
FIG. 1 illustrates a known arterial and venous access configuration.
Figure 2:
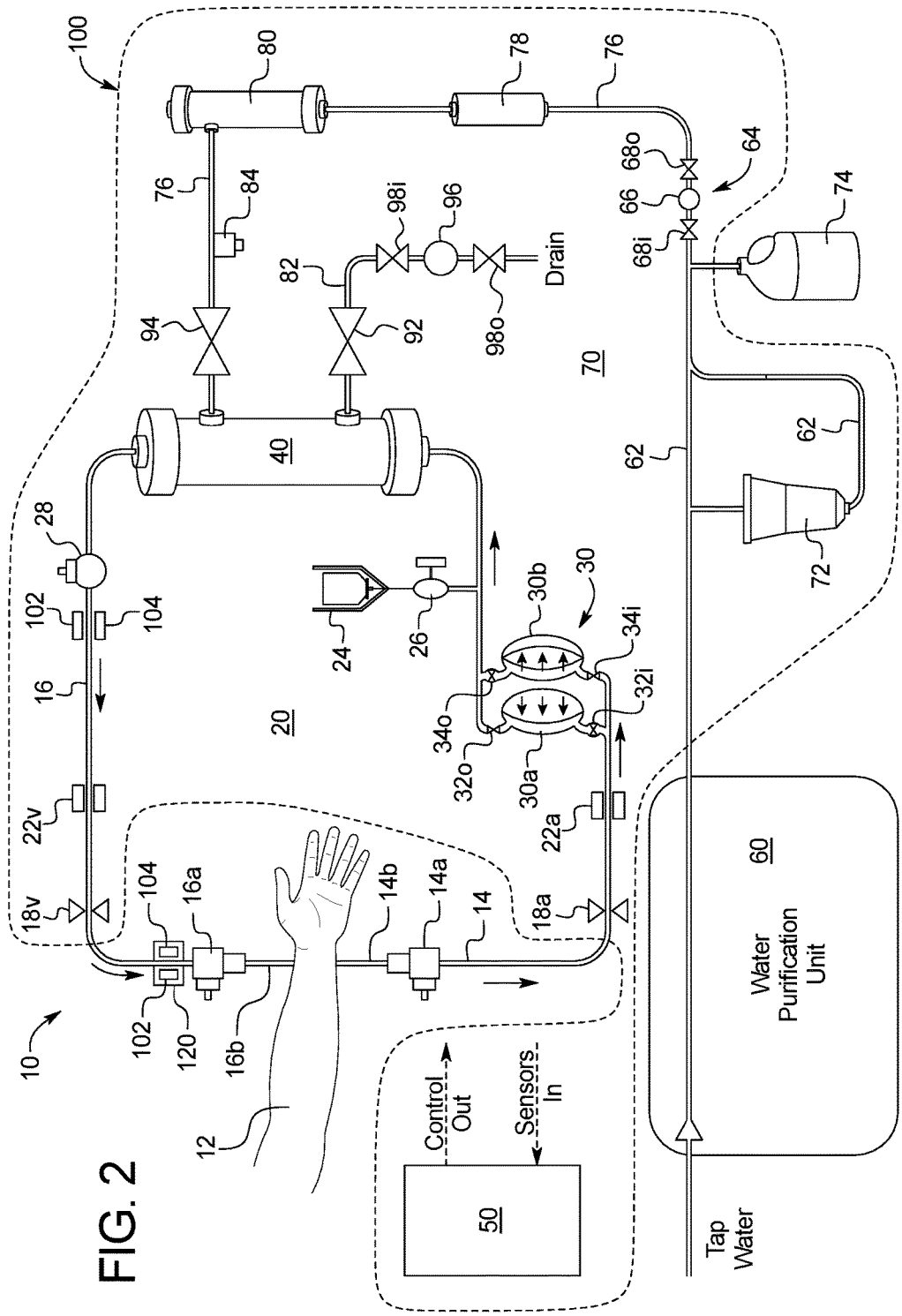
FIG. 2 is a schematic illustration of one embodiment of a renal failure therapy system having an access disconnection system and method of the present disclosure.

Referring now to FIG. 2, one embodiment for a renal failure therapy system 10 having the access disconnection system and method of the present disclosure is illustrated using an HD machine. Generally, system 10 is shown having a very simplified version of the dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

System 10 of FIG. 2 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw flow communication with patient 12. Venous line 16 includes a venous line connector 16a that connects to a venous needle 16b, which is in blood return flow communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 20a and 20v look for air in the arterial and venous lines 14 and 16, respectively. If air is detected by one of air detectors 22a and 22v, system 10 closes line clamps 18a and 18v, pauses the blood and dialysis fluid pumps and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 can be a pneumatic pump or a syringe pump (e.g., stepper motor driven syringe pump) Supplying heparin upstream of blood filter 40 helps to prevent clotting of the blood filter membranes.

A control unit 50 includes one or more processor and memory. Control unit receives air detection signals from air detectors 22a and 22v (and other sensors of system 10, such as temperature sensors, blood leak detectors, conductivity sensors, pressure sensors, and in an embodiment, the access disconnection transducers of the present disclosure), and controls components such as line clamps 18a and 18v, blood pump 30, heparin pump 26, and the dialysis fluid pumps (described below).

Blood exiting blood filter 40 flows through an airtrap 28. Airtrap 28 removes any air from the blood before the dialyzed blood is returned to patient 12 via venous line 16. Airtrap 28 can also have a pierceable septum that allows blood samples to be removed from blood circuit 20.

With the hemodialysis version of system 10 of FIG. 2, dialysis fluid or dialysate is pumped along the outside of the membranes of blood filter 40, while blood is pumped through the insides of the blood filter membranes. Dialysis fluid or dialysate is prepared beginning with the purification of water by water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structure to purify tap water (e.g., remove pathogens and ions such as chlorine) so that the water is in one implementation below 0.03 endotoxin units/ml ("EU/ml") and below 0.1 colony forming units/ml ("CFU/ml"). Water purification unit 60 can be provided in a housing separate from the housing of the hemodialysis machine, which includes blood circuit 20 and a dialysis fluid circuit 70.

Dialysis fluid circuit 70 is again highly simplified in FIG. 2 to ease illustration and to better highlight blood circuit 20. Dialysis fluid circuit 70 in actuality can include all of the relevant structure and functionality set forth in the publications incorporated by reference above. Certain features of dialysis fluid circuit 70 are illustrated in FIG. 2. In the illustrated embodiment, dialysis fluid circuit 70 includes a to-blood filter dialysis fluid pump 64. Pump 64 is in one embodiment configured the same a blood pump 30. Pump 64, like pump 30, includes a pair of pump pods, which again can be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump 96, like pump 64, located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, can be single pod pumps because continuous pumping is not as important in mixing line 62 because there is a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when the HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a tube.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 2 also illustrates that dialysis fluid is pumped along a fresh dialysis fluid line 76, through a heater 78 and an ultrafilter 80, before reaching blood filter 40, after which the used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural valves, and a dialysis fluid holding tank, all illustrated and described in detail in the publications incorporated by reference above.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 can be reused. In one implementation, blood circuit 20 including blood filter 40 are hot water disinfected and reused daily for about one month, while dialysis fluid circuit 70 is hot water disinfected and reused for about six months.

In alternative embodiments, or for CRRT for example, multiple bags of sterilized dialysis fluid or infusate are ganged together and used one after another. In such a case, the emptied supply bags can serve as drain or spent fluid bags.

The machine 100 of system 10 includes an enclosure as indicated by the dotted line of FIG. 2. The enclosure of machine 100 varies depending on the type of treatment, whether the treatment is in-center or a home treatment, and whether the dialysis fluid/infusate supply is a batch-type (e.g., bagged) or on-line.

FIG. 2 illustrates that machine 100 can be provided with a transmitter 102 and a receiver 104, which are held in a common housing, and which straddle and contact venous line 16. In one illustrated embodiment, the transmitter 102 and the receiver 104 are located inside the machine 100. In another illustrated embodiment, the transmitter 102 and the receiver 104 are located outside the machine 100 in a remote or separate unit 120, which may communicate with the machine 100, for example, as discussed in greater detail below. In the illustrated embodiment, transmitter 102 and receiver 104 are configured similar to air detector 22v, wherein transmitter 102 resides on one side of venous line 16, while receiver 104 resides on the opposing side of venous tube 16. Transmitter 102 and receiver 104 are positioned close enough to each other to clamp venous line 16 in place. In an alternative embodiment, receiver 104 is located in a different housing and at a different location from transmitter 102.

Figure 3:
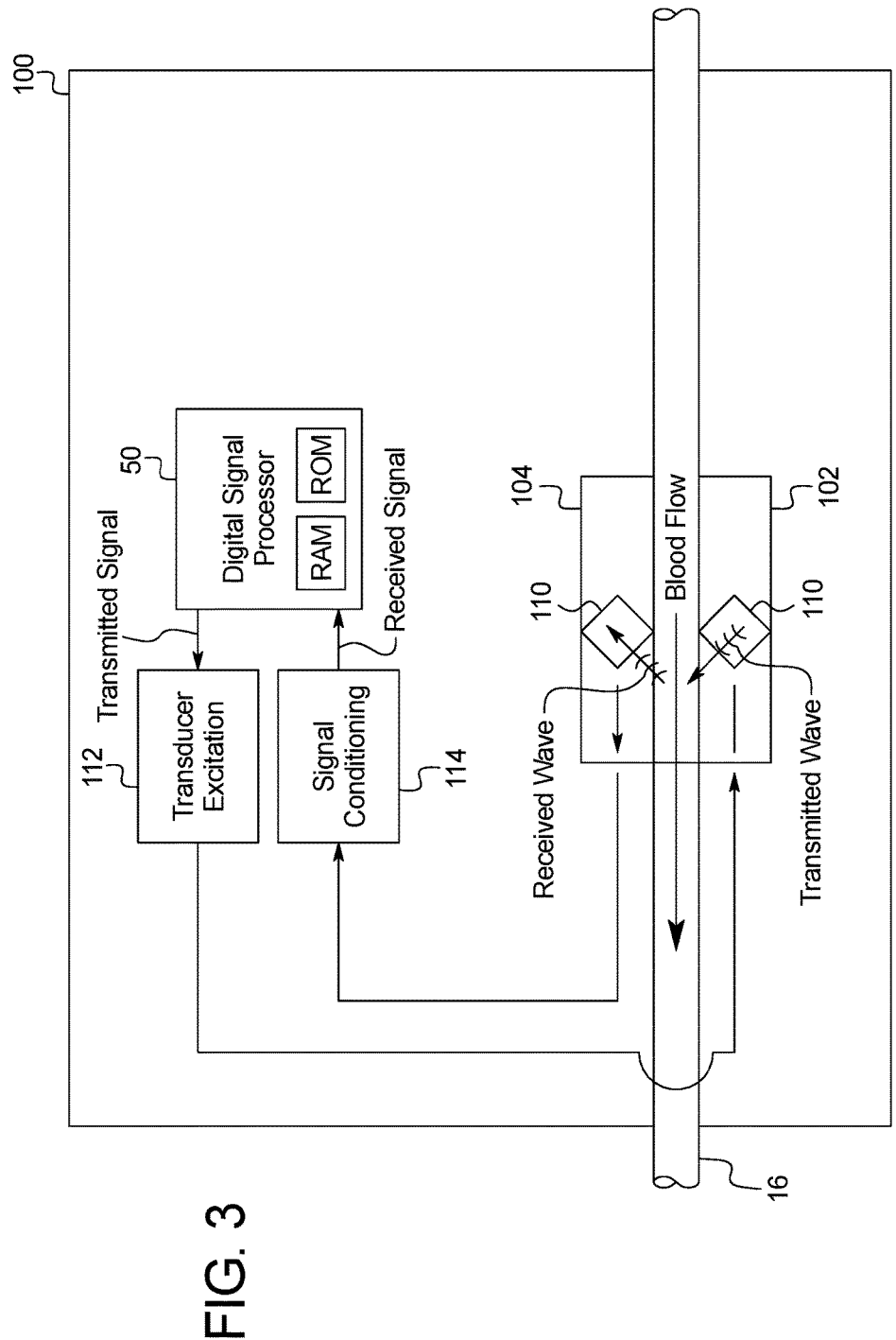
FIG. 3 is a schematic view illustrating an embodiment of the transmitter and receiver and associated electronics of the present disclosure in more detail.

Referring now to FIG. 3, transmitter 102 and receiver 104 each includes a transducer 110. Transducers 110 in one embodiment include a piezoelectric crystal. Transducers 110 in general transmit power from one type of system to another, e.g., from an electrical signal to a mechanical vibration and vice versa. In the piezoelectric embodiment, power is provided to piezoelectric crystal of transducer 110 of transmitter 102 in the form of electricity. FIG. 3 illustrates a transducer excitation apparatus 112, which applies an electrical field to the piezoelectric crystal of transducer 110. The piezoelectric crystal undergoes mechanical deformation due to the electric field. In this manner, the crystal is induced to resonate (vibrate) at a certain frequency to produce ultrasonic waves. In an embodiment, the crystal vibrates at a desired acoustic or ultrasonic frequency, which can be anywhere from 10 Hertz to 100 MegaHertz. The acoustic or ultrasound waves of the piezoelectric crystal of transducer 110 of transmitter 102 are imparted to and travel through blood flowing through venous line 16.

Transmitter 102 in the illustrated embodiment is positioned in parallel with venous line 16 tube. The piezoelectric crystal of transducer 110 on the other hand may be placed at an angle, e.g., forty-five degrees, relative to the venous line 16 tube to produce acoustic or ultrasound waves having a directional component towards venous needle 16b. The emitted signal travels down venous line 16 tube and reflects off of patient 12 at the access of venous needle 16b. The reflected signal travels back up venous line 16 and excites transducer 110 of receiver 104, which is likewise a piezoelectric crystal in one embodiment. Transducer 110 of receiver 104 outputs a corresponding electrical signal. In the illustrated embodiment, transducer 110 of receiver 104 is also mounted at an angle, e.g., forty-five degrees, relative to venous line 16 tube.

The reflected waves apply mechanical stress to transducer 110 of receiver 104, causing the crystal of the transducer to become electrically charged and to vibrate at its resonant frequency. The reflected acoustic or ultrasound waves may have a different frequency than do the emitted acoustic or ultrasound waves, an effect known as the Doppler effect. The change in frequency is dependent on the speed and direction of movement of blood flowing though the access site and whether or not venous needle 16b is properly inserted into patient 12. As discussed in detail below, the electronics in system 10 stores software that processes the received echoes to determine whether or not venous needle 16b is properly inserted into patient 12.

In an alternative embodiment, a single transducer 110 is provided for both transmitter 102 and receiver 104, in which case a second piezoelectric crystal is not needed. Here, transducer 110 is used at one time as transmitter 102 and at another time as receiver 104.

FIG. 3 also shows an embodiment of the electronics associated with system 10. A digital signal processor ("DSP") 50, which can include onboard random access memory ("RAM") and read only memory ("ROM"), sends an output signal to transducer excitation apparatus 112. Excitation apparatus 112 excites the crystal of transducer 110 of transmitter 102 as described above. Reflected waves cause receiver crystal of transducer 110 of receiver 104 (or the crystal of transducer 110 operating as both emitter and receiver) to vibrate and create an acoustic or ultrasound wave, which is sent to signal conditioning 114. Signal conditioning 114 in one embodiment includes an analog to digital ("A/D") converter, which digitizes the reflected wave into a form that DSP 50 can process. Signal conditioning 114 may, in another embodiment, contain demodulation circuitry to separate the signal components in a manner useful for Doppler calculations, for example.

DSP 50 using onboard software described in detail below detects a flow or access condition, a no-flow or full-access disconnection condition or a partial-flow or partial access disconnection condition.

Figure 4:
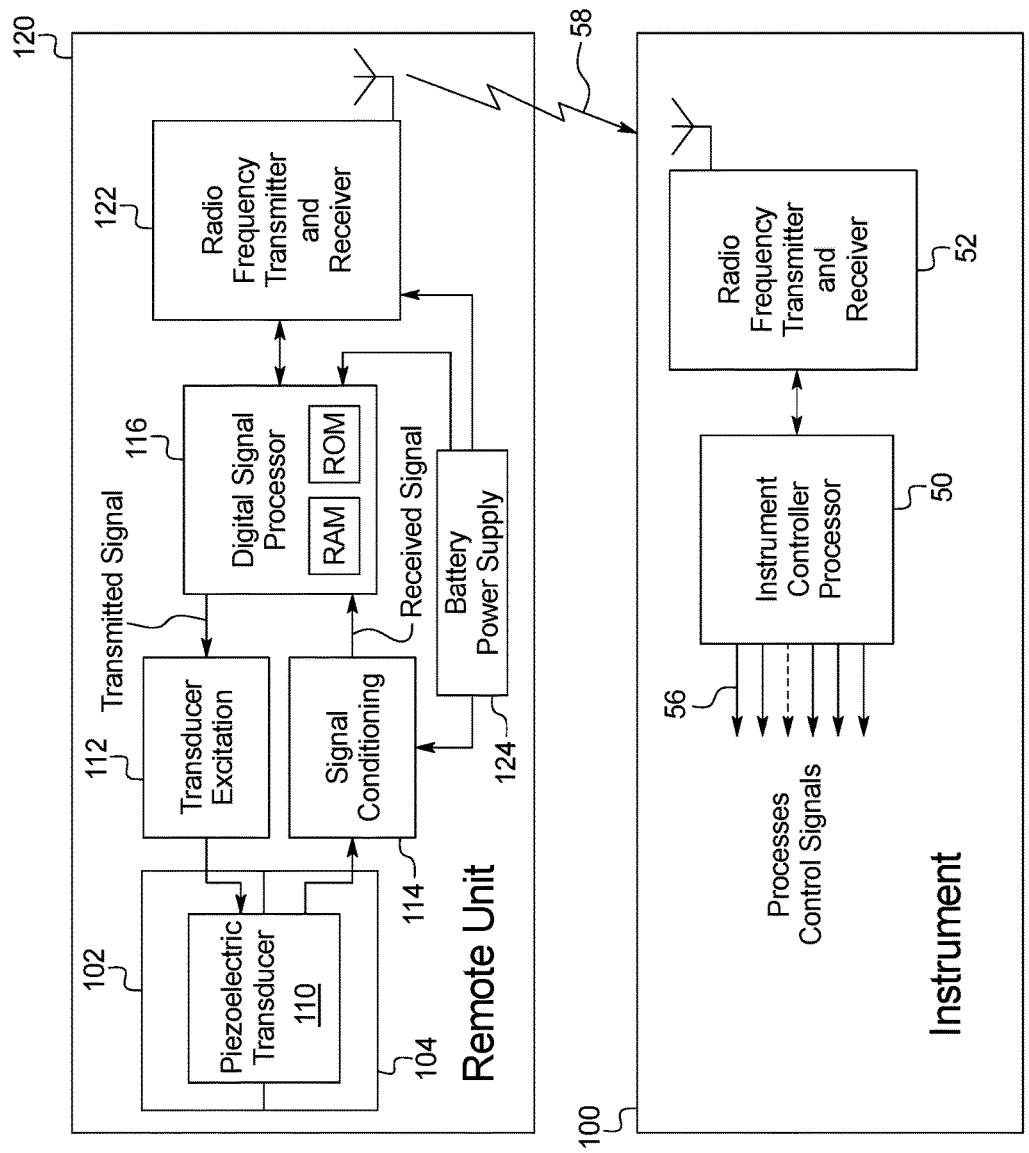
FIG. 4 is a schematic view illustrating another embodiment of the transmitter and receiver and associated electronics of the present disclosure in more detail.

FIG. 4 illustrates an alternative embodiment in which transmitter 102 and receiver 104 are not mounted on the enclosure of machine 100 but are instead clamped, wrapped about or otherwise fixed mechanically to venous line 16, for example closer to venous line connector 16a of venous line 16, which connects to a venous needle 16b. Here, transmitter 102 and receiver 104 are provided in a separate unit 120 having clamping structure or hook and pile flaps that wrap about venous line 16. In the illustrated embodiment, separate unit 120 also houses transducer excitation apparatus 112, signal conditioning 114 and a separate digital signal processor ("DSP") 116, having its own onboard RAM and ROM. Remote DSP 116 communicates back and forth with a remote or wireless emitter/receiver 122, such as a radio frequency ("RF") transmitter/receiver. Other remote signals may be used alternatively, such as microwave signals. Further alternatively, unit 120 is hard-wired to machine 100 and communicates via electrical signals, e.g., 4 to 20 mA or 0 to 5 VDC signals.

Machine 100 houses a wireless transmitter/receiver 52, such as an RF transceiver. In system 10, wireless transmitter/receiver 52 of machine 100 sends messages to and receives messages from the remote unit 120 via its wireless transmitter/receiver 122. Machine wireless transmitter/receiver 52 in turn communicates back and forth with a central processing unit ("CPU") 50 located within machine 100. CPU 50 in an embodiment is a supervisory processor that communicates via signals 56 with one or more delegate processor and circuit board or controller located within machine 100. Transducers 110, signal conditioning 114, excitation apparatus 112, DSP 116 and transmitter/receiver 122 may be located on a printed circuit board ("PCB") in one embodiment. The PCB can be located within remote unit 120, or within a separate housing (not illustrated). In an alternative embodiment, DSP 116 and its associated functionality are located and performed, respectively, at CPU 50.

In the illustrated embodiment, remote unit 120 also includes a battery, a power supply or a combination of both, referred to generally herein as power supply 124. Supply 124 can be a rechargeable battery, for example. Supply 124 powers the components of remote unit 120, such as, signal conditioning 114, DSP 116 and wireless communicator 122. Power supply 124 may be coupled to an audio, visual or audiovisual alarm that alerts the patient when the power supply needs to be recharged or replaced.

In the embodiment illustrated in FIG. 4, remote wireless communicator or transceiver 122 communicates with instrument communicator 52 via an RF signal 58. Signal 58 can be any of the following types: an electrical signal, a radio frequency signal, a microwave signal, a continuous signal, an intermittent signal, a signal sent only upon the sensing of the change and any suitable combination thereof. Signal 58 may be a continuous e.g., digitalized, data stream, which CPU 50 my use to determine that an access disconnection event has occurred. If an access disconnection occurs, the frequency and/or other characteristics of the reflected acoustic or ultrasonic waves may change significantly enough as does the output of DSP 116 and corresponding signal 58 that the software within CPU 50 determines that a partial or full access disconnection has occurred. When an access disconnection event is detected, CPU 50 via signals 56 causes other components within machine 100 to take appropriate action, e.g., causes an audio, visual or audiovisual alarm to appear on and/or be sounded from a graphical user interface of machine 100. CPU 50 also likely causes blood pump 30 to shut down, occludes or closes blood line valves 18a and 18v, and puts the machine into a safe mode. Patient 12 may be allowed to try to reinstate venous access and continue treatment or be told to disconnect completely from the machine.

In an alternative embodiment, the processing of the reflected waves is done at remote unit 120. Here, remote DSP 116 determines whether an access disconnection event has occurred. Remote DSP 116 sends such determination, e.g., wirelessly via transceivers 122 and 52 to CPU 50 at predetermined intervals or when CPU 50 requests such information. When an access disconnection is detected, CPU 50 causes other components within machine 100 to take appropriate action as described above. Thus wireless signal 58 can be a continuous signal, an intermittent signal or a signal sent only upon the sensing of the change and any suitable combination thereof.

In a further alternative embodiment, remote unit 120 sounds its own audio, visual or audiovisual alarm, which alerts a patient of an access disconnection. In this embodiment, remote unit 120 may or may not communicate with the renal failure therapy machine. For example, remote unit 120 can sound an alarm, while the machine shuts down one or more pumps, occludes or closes blood line valves 18a and 18v and places itself into a safe mode.

It should therefore be appreciated that the signal metrics described next can be performed on main CPU 50 of machine 100 or on remote DSP 116 of remote unit 120. Alternatively, the signal metrics described next are performed on both CPU 50 and a separate safety processor (not illustrated) as redundant ADS check. CPU 50 and the separate safety processor receive the incident and reflected electrical signals in parallel in one embodiment. Here, if either CPU 50 or the separate safety processor detects an access disconnection, machine 100 alarms, goes into a safe mode, shuts down blood pump 30, closes blood clamps 18a and 18v, etc.

System Methodology

Referring now to FIG. 5, an embodiment of a signal metrics method 150 performed at one or more of the processors discussed above is illustrated. At oval 152, method 150 begins.

At block 154, processor 50, 116 converts the transmitted (incident) and received (reflected) acoustic ultrasound wave signals into the frequency domain, e.g., via taking the Fast Fourier transform of the signals. The transmitted or incident signal is the electrical signal commanded by the processor 50, 116 to cause transducer excitation 112 to excite transducer crystal 110 of transmitter 102 to vibrate at a desired acoustic or ultrasound frequency. The received or reflected signal is the electrical signal that is outputted by transducer crystal 110 of receiver 104 based upon a reflected acoustic or ultrasound wave received at the transducer crystal. In an example embodiment, the transmitted (incident) signal may be produced by a single excitation of a magnetic transducer, e.g., by a single wave of a sine or cosine cycle at 30 Hz. For example, the transmitted (incident) signal may be continuously repeated on a 500 millisecond ("msec") interval, which may provide ample processing time after receiving the received (reflected) signal (e.g., using the Fast Fourier transform), while also providing adequate response time for the system to react to an access disconnect. The Fourier transform as is known in the art converts the transmitted and received signals from a time-based domain to a frequency domain. The Fourier transform results in a complex-valued function for each signal. That is, the results will have real and imaginary parts.

At block 156, processor 50, 116 extracts a spectral value at a specified frequency for each of the converted transmitted (incident) and received (reflected) signals, e.g., using the transmitted and received signals' Fourier transform spectra. In an example embodiment, a spectral value is extracted at a specified frequency (e.g., 10 Hz) using a complex-valued function resulting from taking the Fast Fourier transform as discussed above. Each spectral value may include both real and imaginary parts.

In an example embodiment, the specified frequency, which may typically be about 10 Hz to 12 Hz, may be empirically determined based on a peak in a power spectrum of a raw venous line pressure signal, which may be calculated using signals converted into the frequency domain in the same manner as discussed above. For example, the particular equipment being used and/or the flowrates being used may provide more robust results at a specified frequency other than 10 Hz to 12 Hz. It should be appreciated that many variables may impact extracted spectral values, such as blood flow rates and/or equipment specifications (e.g., tubing and needle sizes). For example, blood flowrates may vary (e.g., 0 to 800 mL/min) for different equipment, different patients, and/or different treatment regimens, as well as during the course of any given treatment. A specified frequency may therefore be predetermined based upon typical flowrates (e.g., 50, 100, 200, 400, 600 or 800 mL/min) for a particular machine, equipment, patient, and/or treatment regimen. Also, a specified frequency may be dependent on a current blood flow rate, e.g., the specified frequency may be set at 10 Hz during low flow and 12 Hz during high flow.

At block 158, processor 50, 116 calculates a reflection coefficient (R) and an impedance ratio (I) based on the extracted spectral values for the converted transmitted (incident) and received (reflected) signals. The reflection coefficient (R) and the impedance ratio (I) may be calculated, for example, based on the following equations, where $p_r$ is an extracted spectral value for reflected pressure, and $p_i$ is an extracted spectral value for incident pressure:

$$R = \frac{p_r}{p_i}$$
$$I = \frac{p_i + p_r}{p_i - p_r} = \frac{1 + (p_r/p_i)}{1 - (p_r/p_i)} = \frac{1 + R}{1 - R}$$

At block 160, processor 50, 116 determines the real and imaginary parts for each of reflection coefficient (R) and an impedance ratio (I). Here, because R and I are calculated from complex components (the real and imaginary parts from the extracted spectral values from the Fourier transform), R and I are both complex too, each having a real part and an imaginary part. Thus, since $p_r$ and $p_i$ are both complex values (e.g., x+iy), based on the equations shown above, R and I will also be complex values.

At block 162, processor 50, 116 determines the magnitude and phase shift of (a) the reflection coefficient (R) and (b) the impedance ratio (I). The magnitudes and phase shifts of the reflection coefficient (R) and the impedance ratio may be determined using the real and imaginary parts of the reflection coefficient (R), and the real and imaginary parts of the impedance ratio (I), respectively. For example, magnitude may be determined as the square root of the sum of the real part squared and the imaginary part squared, and phase shift may be determined as the arctangent of the quotient of the imaginary part divided by the real part.

At diamond 164, processor 50, 116 uses data from at least one of (i) the imaginary part of R or (ii) the imaginary part of I to determine if an access disconnection has occurred. Processor 50, 116 may use either (i) or (ii) or both (i) and (ii) to determine if an access disconnection has occurred. Processor 16 may use either (i) or (ii) or both (i) and (ii) in combination with any one or more of (iii) phase shift of I, (iv) phase shift of R, (v) real part of R, (vi) real part of I, (vii) magnitude of R, or (viii) magnitude of I to determine if an access disconnection has occurred. As illustrated below, (i) to (iv) provide the best signal to noise ratios.

At block 166, if an access disconnection has occurred, processor 50, 116 takes corrective measures, e.g., causes at least one machine 100 to alarm, go into a safe mode, shut down blood pump 30, close blood clamps 18a and 18v, etc. Please note that an access disconnection or access disconnection event may include a full or partial dislodgement of the needle from patient 12.

At diamond 168, if an access disconnection has not occurred, processor 50, 116 determines whether treatment has ended. If treatment has not ended, processor 50, 116 returns to block 154 and repeats the steps of blocks 154 to 164. The loop between block 154 to diamond 168 continues (system 10 continuously looks for an access disconnection or at a specified cycle frequency) until an access disconnection has occurred, after which corrective action is taken at block 166, or treatment ends as determined at diamond 168, after which method 150 ends, as illustrated at oval 170. As discussed herein, corrective action may include any one or more of providing an audio, visual or audio-visual alarm, closing one or more line clamp, shutting down one or more pump, e.g., the blood pump, placing the machine in a safe mode until the access disconnection can be fixed, and/or shutting treatment down completely.

The loop between block 154 to diamond 168 may occur, for example, every 500 msec (2 Hz), or at any other suitable frequency (e.g., 0.5 Hz to 10 Hz). It should be appreciated that the frequency interval for completing the loop between block 154 and diamond 168 may be selected to provide an adequate amount of time to receive the reflective signals and to complete processing of the transmitted and received signals, as well as an adequate response time for determining an access disconnect. The frequency between block 154 and diamond 168 is also chosen so as to prevent an unacceptable level of false positives, thereby advantageously resulting in a robust access disconnect system.

Figure 6A:
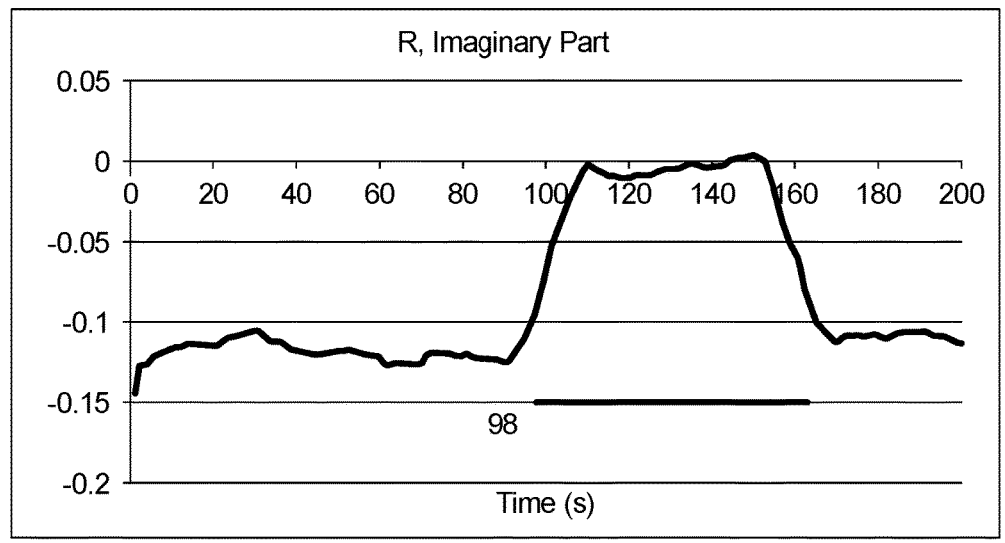
FIGS. 6A to 6H are plots of various signal metrics obtained from a test of the methodology of FIG. 5.

FIGS. 6A to 6H illustrate results of a test performed mimicking the pertinent structure of system 10 illustrated and described above, including the use of a transducer excited with a single sinusoidal wave cycle at 30 Hz to create transmitted (incident) and received (reflected) signals for an acoustic wave every 500 msec. The flowrate was set at a common value for a renal failure therapy in a low flow mode, namely, 50 mL/min. In the test, a needle dislodgement mimicking a venous needle dislodgement was simulated at about time equaling 90 to about 150 seconds after the beginning of the test illustrated in the plots. Method 150 described above was performed over a time from zero to about 200 seconds and generated the following eight plots: FIG. 6A imaginary part of R, FIG. 6B imaginary part of I, FIG. 6C phase shift of R, FIG. 6D phase shift of I, FIG. 6E real part of R, FIG. 6F real part of I, FIG. 6G magnitude of R, and FIG. 6H magnitude of I.

Figure 6B:
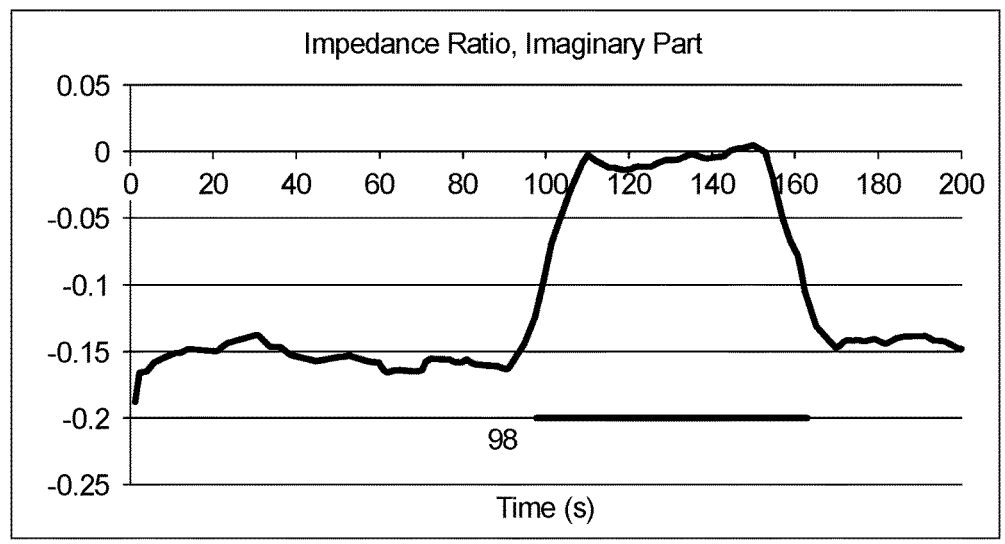
Figure 6C:
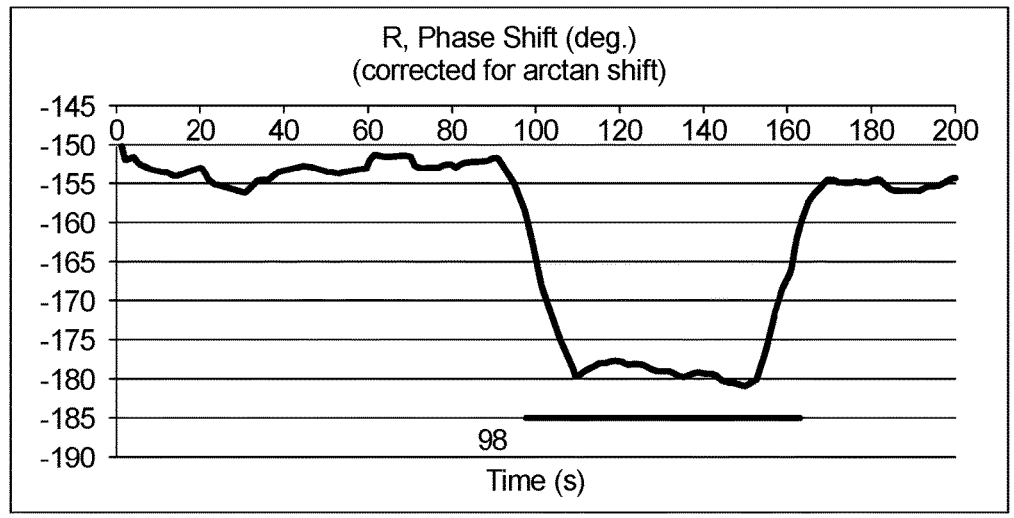
Figure 6D:
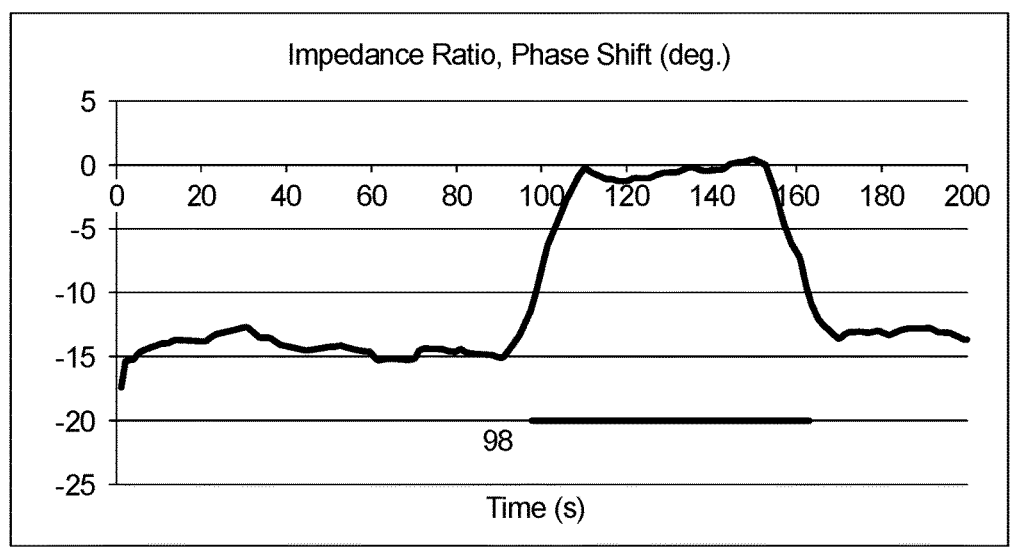
Figure 6E:
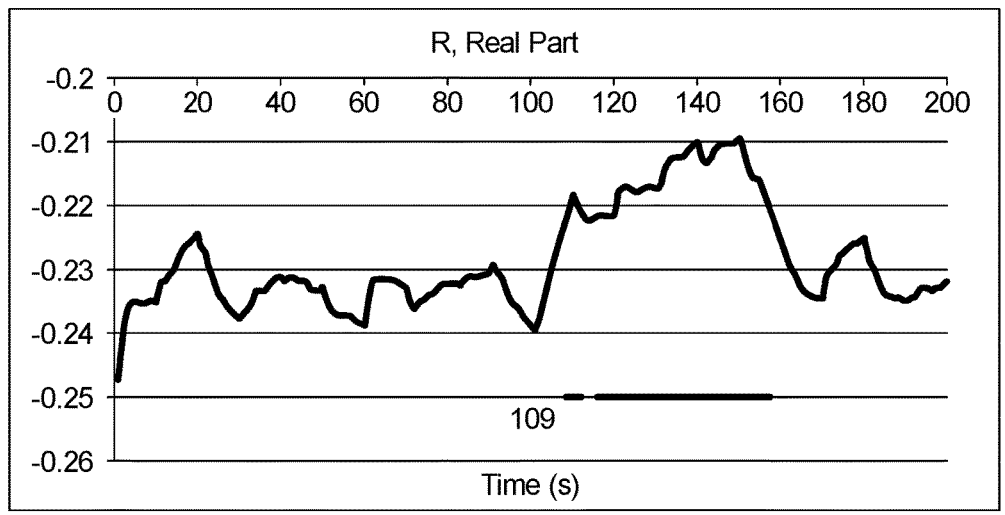
Figure 6F:
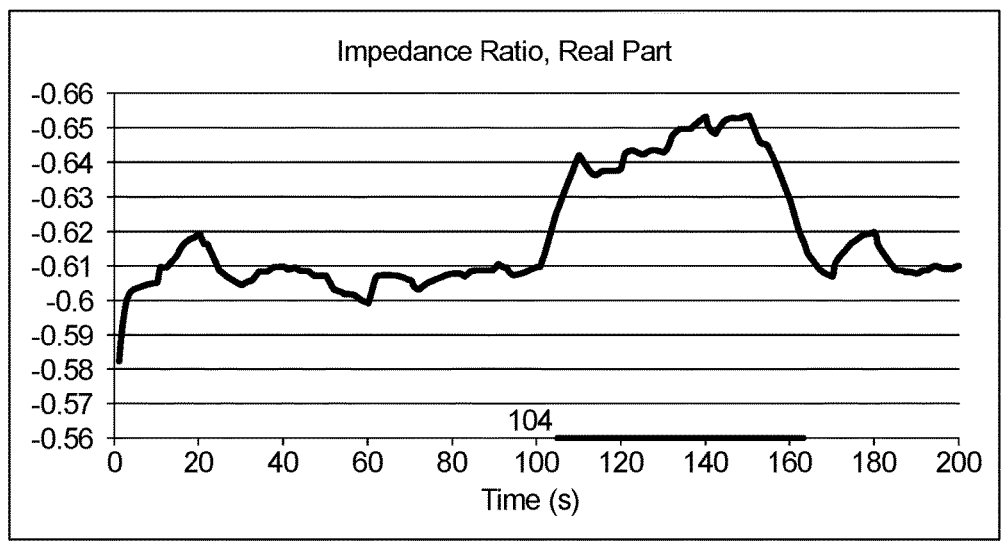
Figure 6G:
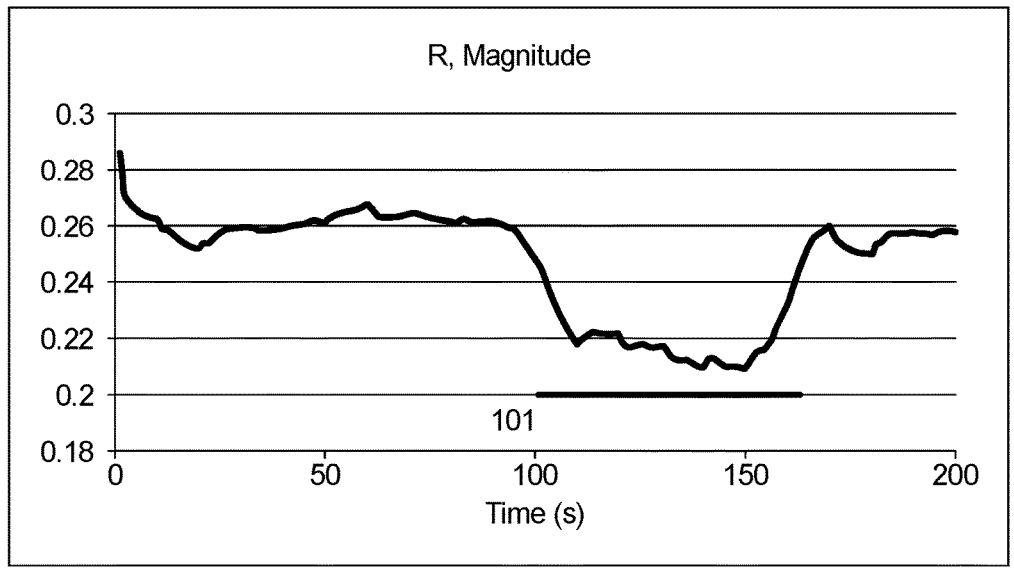
Figure 6H:
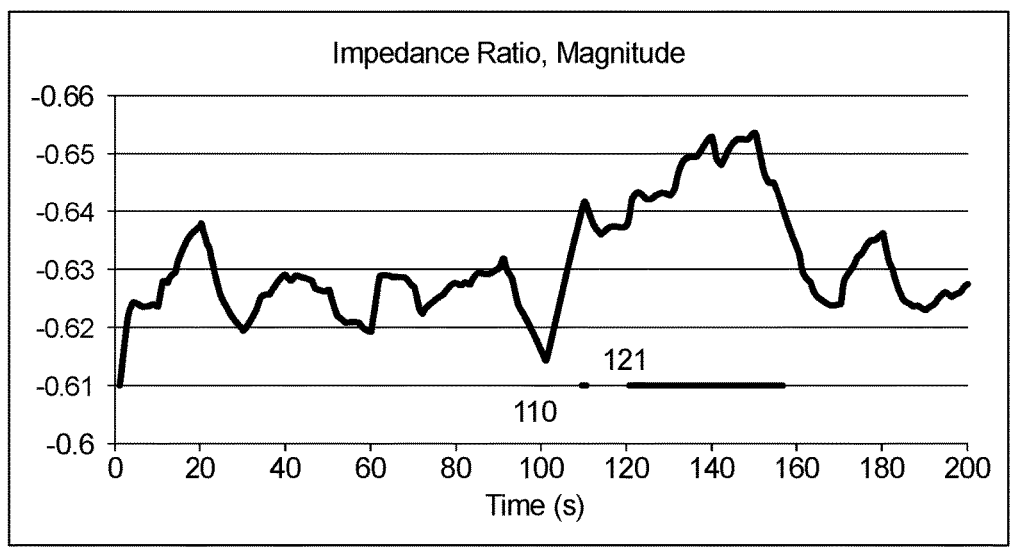

FIG. 6A imaginary part of R, FIG. 6B imaginary part of I, FIG. 6C phase shift of I, and FIG. 6D phase shift of R showed the best signal to noise ratios, however, the needle dislodgement was detected in each of the plots of FIGS. 6A to 6H. Again, it is contemplated that processor 50, 116 be configured to look at the data of the plots of FIG. 6A and/or FIG. 6B, or FIG. 6A and/or FIG. 6B in combination with any one or more of the data of plots of FIGS. 6C to 6H to determine if an access disconnection has occurred. In an embodiment, data from at least one of the plots of FIG. 6A or FIG. 6B is analyzed.

Using multiple plots provides redundancy and may help to prevent false triggers. In one example, the data from four plots (FIG. 6A, FIG. 6B, FIG. 6C and FIG. 6D) is analyzed in parallel to look for an access disconnection. Processor 50, 116 may be programmed to signal an access disconnection event when (a) any one of the four sets of data indicates disconnection, (b) two of the four sets indicate disconnection, (c) three of the four sets indicate disconnection or (d) all four sets indicate disconnection. Variations (a) to (d) vary from most sensitive (good for detection, but bad for false triggering) to least sensitive (good for preventing false triggering).

In various embodiments, processor 50, 116 may be configured to store a value for the y-axis of the plots of FIGS. 6A to 6H (FIGS. 6A, 6B and 6E to 6H are unitless, while phase shift in FIGS. 6C and 6D is measured in degrees). If the calculated value is different from the stored value by more than a certain amount, processor 50, 116 determines that an access disconnection has occurred. The stored (compared against) value may be common for all patients, be selected for each patient, or be selected for each of different groups of patients. In an alternative embodiment, processor 50, 116 determines the stored value at the beginning of each treatment. Knowing that different patients and different treatments can produce different plots, processor 50, 116 of system 10 may use the beginning of treatment, when it is assumed that needle access is good, to establish a baseline comparison value, which is then compared against with the calculated values over the rest of the treatment. For example, the baseline value may be determined for a period of 30 seconds at the beginning of each treatment, or for any suitable period of time (e.g., 10 seconds, 60 seconds, 90 seconds). In an embodiment, a separate baseline valve is determined for each of the plots of 6A to 6H used in the access disconnection evaluation.

Alternative Embodiments

Many alternative embodiments have been discussed above. The following list summarizes some of the above and adds additional alternative embodiments. As discussed above, transmitter 102 and receiver 104 can be located at machine 100 or remote from machine 100, along venous line 16. Method 150 may be performed at machine CPU 50, at remote sensing processor 116, or using both processors. Also, while system 10 and method 150 are primarily concerned with venous line 16 disconnection, they may be applied alternatively or additionally to arterial line 14 disconnection.

Redundant Access Disconnection/Blood Leak Detection System

Certain known access disconnection systems rely on the breaking of an electrical circuit to detect an access problem. One problem with these systems is that a needle dislodging from the patient does not always break the electrical circuit. A venous needle can for example dislodge from the patient but direct the flow of blood over the access from which the needle has been dislodged or over the other (e.g., arterial) needle to complete or re-complete the electrical circuit. Here, blood would not be returned to the patient but no alarm would sound.

To address the above-described problem, it is contemplated to combine the acoustic or ultrasound systems described herein with an electrical impedance type of system, such as one of the impedance systems of the '098 and '480 Patents. Either system can detect an access disconnection and cause machine 100 to alarm, go into a safe mode, shut down blood pump 30, close blood clamps 18a and 18v, etc.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A renal failure therapy system comprising:
a blood filter;
a blood pump in fluid communication with the blood filter;
a dialysis fluid pump in fluid communication with the blood filter;
a blood line for connection to a patient, the blood line in fluid communication with the blood filter;
a transmitter positioned and arranged to receive a transmit signal and to transmit a wave into blood flowing through the blood line, the wave based on the transmit signal;
a receiver positioned and arranged to receive the wave and to emit a received signal based on the received wave; and
at least one processor for initiating the transmit signal and for receiving the received signal, the processor configured to
convert the transmit and received signals into a frequency domain,
extract spectral values for the converted transmit and received signals,
calculate a real part and an imaginary part of at least one of a reflection coefficient (R) or an impedance ratio (I) using the spectral values,
determine at least one first baseline value for the imaginary part of at least one of R or I at a beginning of a treatment,
determine at least one second baseline value for the real part of at least one of R or I at the beginning of the treatment, and
compare the imaginary part of at least one of R or I to the at least one first baseline value and compare the real part of at least one of R or I to the at least one second baseline value to determine if an access disconnection event concerning fluid communication between the blood line and the patient has occurred.

2. The renal failure therapy system of claim 1, wherein the at least one processor analyzes imaginary parts of both the reflection coefficient (R) and the impedance ratio (I) to determine if an access disconnection event concerning fluid communication between the blood line and the patient has occurred.

3. The renal failure therapy system of claim 1, wherein the at least one processor further analyzes at least one of a phase shift of at least one of R or I or a magnitude of at least one of R or I to determine if an access disconnection event concerning fluid communication between the blood line and the patient has occurred.

4. The renal failure therapy system of claim 3, wherein the phase shift is provided as an angular value in degrees.

5. The renal failure therapy system of claim 1, wherein the at least one processor determines the at least one first baseline value and the at least one second baseline value for a period of at least 30 seconds from the beginning of the treatment.

6. The renal failure therapy system of claim 1, wherein the spectral values are calculated at a specified frequency.

7. The renal failure therapy system of claim 6, wherein the specified frequency is in a range of 10 Hz to 12 Hz.

8. The renal failure therapy system of claim 6, wherein the specified frequency corresponds to a frequency at a peak spectral value.

9. The renal failure therapy system of claim 1, wherein the at least one processor determines the at least one first baseline value and the at least one second baseline value for analysis during a period of time at the beginning of the treatment.

10. The renal failure therapy system of claim 1, wherein the converted transmit and received signals each include real and imaginary parts, leading to the imaginary parts of R and I.

11. The renal failure therapy system of claim 1, wherein the imaginary parts of the reflection coefficient (R) and the impedance ratio (I) are provided as unitless numerical values.

12. The renal failure therapy system of claim 1, which is a plasmapherisis, hemodialysis ("HD"), hemofiltration ("HF"), hemodiafiltration ("HDF") or continuous renal replacement therapy ("CRRT") system, and wherein the blood filter is a dialyzer or hemofilter.

13. The renal failure therapy system of claim 1, wherein the blood filter, the blood pump, and the dialysis fluid pump are housed in a machine, and the transmitter and the receiver are housed in a separate unit that communicates wirelessly with the machine.

14. The renal failure therapy system of claim 1, wherein the blood filter, the blood pump, and the dialysis fluid pump are housed in a machine, and the transmitter and the receiver are located at the machine.

15. The renal failure therapy system of claim 1, wherein the at least one processor is part of a housing for the transmitter and the receiver, the housing configured to be attached to the blood line.

16. The renal failure therapy system of claim 1, wherein the at least one processor is a first processor, and which includes a second, redundant at least one processor for receiving the transmit and received signals, the second processor configured to convert the transmit and received signals into the frequency domain, extract spectral values for the converted transmit and received signals, calculate at least one of the reflection coefficient (R) or the impedance ratio (I) using the spectral values, and analyze the imaginary part at least one of R or I to determine if the access disconnection event concerning fluid communication between the blood line and the patient has occurred.

17. The renal failure therapy system of claim 1, wherein the blood line is a venous blood line.

18. The renal failure therapy system of claim 1, wherein the at least one processor is configured to perform at least one of: (i) shutting down a blood pump, (ii) activating a venous line clamp, and (iii) alerting the patient of the disconnection upon the disconnection event.

19. The renal failure therapy system of claim 1, wherein the transmitter and the receiver are of at least one type selected from the group consisting of: a single transducer, multiple transducers, piezoelectric, electromagnetic, or any suitable combination thereof.

20. The renal failure therapy system of claim 1, wherein the disconnection event includes an output of at least one type selected from the group consisting of: an electrical output, a radio frequency output, a microwave output, a continuous output, an intermittent output, an output occurring upon the change, a wireless output, or any suitable combination thereof.

21. A renal failure therapy system comprising:
a blood filter;
a blood pump in fluid communication with the blood filter;
a dialysis fluid pump in fluid communication with the blood filter;
a blood line for connection to a patient, the blood line in fluid communication with the blood filter;
a transmitter positioned and arranged to receive a transmit signal and to transmit a wave into blood flowing through the blood line, the wave based on the transmit signal;
a receiver positioned and arranged to receive the wave and to emit a received signal based on the received wave; and
at least one processor for initiating the transmit signal and for receiving the received signal, the processor configured to
convert the transmit and received signals into a frequency domain,
extract spectral values for the converted transmit and received signals,
calculate a real part and an imaginary part of at least one of a reflection coefficient (R) or an impedance ratio (I) using the spectral values,
determine at least one first baseline value for the imaginary part of at least one of R or I at a beginning of a treatment,
determine at least one second baseline value for the real part of at least one of R or I at the beginning of the treatment, and
compare plural ones of (i) the imaginary part of at least one of R or I to the at least one first baseline value, (ii) a phase shift of R, (iii) a phase shift of I, (iv) the real part of at least one of R or I to the at least one second baseline value, (v) a magnitude of R, and (vi) a magnitude of I, and apply an algorithm to the analyzed plural ones of (i) to (vi) to determine if an access disconnection event concerning fluid communication between the blood line and the patient has occurred.

22. The renal failure therapy system of claim 21, wherein the algorithm includes determining that an access disconnection event concerning fluid communication between the blood line and the patient has occurred if at least (i) and (iv) indicate the access disconnection event.

23. The renal failure therapy system of claim 21, wherein the algorithm includes determining that an access disconnection event concerning fluid communication between the blood line and the patient has occurred if each of the plural ones of (i) to (vi) indicates the access disconnection event.

24. The renal failure therapy system of claim 21, wherein the algorithm includes determining an access disconnection event concerning fluid communication between the blood line and the patient has occurred if multiple ones of the plural ones of (i) to (vi) indicate the access disconnection event.

\* \* \* \* \*